United States Patent [19]

Baseman et al.

[11] Patent Number: 5,158,870
[45] Date of Patent: Oct. 27, 1992

[54] DIAGNOSTIC METHODS FOR MYCOPLASMA GENITALIUM INFECTIONS

[75] Inventors: Joel B. Baseman; Janice Morrison-Plummer, both of San Antonio, Tex.

[73] Assignee: Board of Regents, The University of Texas System, Austin, Tex.

[21] Appl. No.: 483,031

[22] Filed: Feb. 16, 1990

Related U.S. Application Data

[63] Continuation of Ser. No. 890,812, Jul. 28, 1986, abandoned.

[51] Int. Cl.$^5$ .................... G01N 33/569; C07K 15/28
[52] U.S. Cl. .................................. 435/7.32; 435/7.9; 435/7.94; 435/240.27; 435/975; 530/388.4; 530/391.3; 530/809; 935/95
[58] Field of Search .............. 435/7.1, 7.32, 7.9, 435/7.92, 7.95, 29, 174, 870, 975, 240.27; 436/501, 518, 527, 531, 536, 538, 542, 548, 21, 808, 811; 530/387, 809; 935/95, 103, 106, 110

[56] References Cited

U.S. PATENT DOCUMENTS 4,666,851  5/1987  Lee ...................................... 435/253

OTHER PUBLICATIONS

Scott, M. G., Trends in Biotechnology, vol. 3, No. 7, 1985, pp. 170–175.
Sevier et al, Clin. Chem., vol. 27(11), 1981, pp. 1797–1806.
Baseman et al. (1984), Infection and Immunity, 43:1103–5.
Lind et al. (1984), J. Clin. Microb., 20:1036–43.
Baseman et al. (1984), Israel J. Med. Sci., 20:866–6.
Hu et al. (1984), Israel J. Med. Sci., 20:916–19.
Tully et al. (1983), Int. J. Systemic Bacteriology, 33:387, 396.
Lind (1982), Lancet, ii:1158–9.
Tully et al. (1981), Lancet, i1288–91.
Clyde and Hu (1986), Inf. and Immun., 51:690–2.
Taylor-Robinson et al. (1985), Genitourinary Med., 61:319–24.
Taylor-Robinson and Furr (1985), J. Med. Biol., 19(3):xiii.
Furr and Taylor-Robinson (1984), J. Clin. Path., 37:1072–4.
Kenny and Cartwright (1984), Israel J. Med. Sci., 20:908–11.
Taylor-Robinson et al. (1983), Lancet, 8323:527.
Morrison-Plummer et al. (1983), J. Immunol. Meth., 64:165–78.

*Primary Examiner*—Esther L. Kepplinger
*Assistant Examiner*—Carol E. Bidwell
*Attorney, Agent, or Firm*—Arnold, White & Durkee

[57] ABSTRACT

Monoclonal antibodies binding *Mycoplasma genitalium* more strongly than *Mycoplasma pneumoniae, Mycoplasma hominis, Mycoplasma orale, Mycoplasma salivarium* and *Acholeplasm laidlawii* are described herein. These monoclonal antibodies are utilized in immunoassays directed toward the detection of *M. genitalium* infections. Hybridomas producing the above-described monoclonal antibodies have been created and isolated. These monoclonal antibodies are directed toward *M. genitalium* antigens. Certain antibodies bind protein antigens, while others bind lipid antigens. In one case a particular antibody apparently has binding affinity for both protein and lipid antigens of *M. genitalium*.

17 Claims, No Drawings

DIAGNOSTIC METHODS FOR MYCOPLASMA GENITALIUM INFECTIONS

BACKGROUND OF THE INVENTION

The present application is a continuation of Applicants' co-pending U.S. application, Ser. No. 890,812, filed Jul. 28, 1986, now abandoned entitled "DIAGNOSTIC METHODS FOR *MYCOPLASMA GENITALIUM INFECTIONS.*" Priority is claimed in the present application from Applicants' referenced co-pending application.

The present invention relates to *Mycoplasma genitalium* and specific immunoassays therefor.

Of the human mycoplasma flora, there are six known species associated with the urogenital tract. *Ureaplasma urealyticum* and *Mycoplasma hominis* are often isolated from the urogenital tract, yet are found in patients with and without urogenital disease. *M. fermentans, M. salivarium*, and *M. pneumoniae* are all human pathogens, yet are only rarely isolated from the urogenital tract and have not been implicated in an etiological role for urogenital disease. In 1981, Tully and co-workers isolated a new species of mycoplasma from two men with non-gonococcal urethritis (Tully, et al. (1981), Lancet i:1288-1291). This new species, *M. genitalium*, shares morphological, ultrastructural and antigenic features with other mycoplasmas (especially *M. pneumoniae*) including a flask-like appearance by electron microscopy, gliding mobility, and a specialized tip organelle capable of mediating adherence of the organism to glass and to sialic acid residues on eukaryotic cells. *M. genitalium's* distinction among the various species has also been established by unique in vitro growth requirements including an enhanced sensitivity to thallium acetate (Tully, et al. *Lancet i*:1288-1291), by restriction enzyme analysis (Baseman, et al. (1984), *Israel J. Med. Sci. V* 20, pp 866-869), and by SDS-gel electrophoresis (Baseman, et al. (1984), *Infect. Immun.*, V 43. pp 1103-1105) (Lind, et al. (1984) *J. Clin. Microbiol.*, V. 20(6) pp 1036-1043).

Because of ultrastructural and morphological similarities of *M. genitalium* to *M. pneumoniae*, extensive serological studies have been performed using polyclonal antibodies. Initial studies by Tully, et al. (Tully, et al. (1981) *Lancet* i:1288-1291) (Tully, et al. (1983) *Inter. J. Syst. Bact.* V 33: pp 387-396) using metabolic inhibition assays indicated little immunocrossreactivity among *M. genitalium* and other mycoplasma species. In contrast, later studies by Lind (Lind, (1982) *Lancet* ii: pp 1158-1159) (Lind, et al. (1984) *J. Clin. Microbiol.* V. 20(6) pp 1036-1043) revealed serological cross-reactions between *M. genitalium* and *M. pneumoniae* using complement fixation, growth inhibition, and metabolic inhibition assays. Radioimmunoassays and SDS-polyacrylamide gel electrophoresis with immune rabbit serum to *M. pneumoniae* and *M. genitalium* have confirmed extensive crossreactivity of proteins between the species (Baseman, et al. (1984), *Infect. Immun.*, V 43, pp 1103-1105) and (Hu, et al. (1984), *Israel J. Med. Sci.*, V 20, pp 916-919). In a recent study by Hu (Hu, et al. (1984), *Israel J. Med. Sci.*, V 20. pp 916-919), one of a group of monoclonal antibodies prepared against the P1 protein of *M. pneumoniae* crossreacted with *M. genitalium*. These data are in conflict to a report by Baseman et al. (Baseman, et al. (1984), *Infect. Immun.*, V 43, pp 1103-1105) where none of the monoclonal antibodies to *M. pneumoniae* protein P1 precipitated proteins of *M. genitalium*. The accumulation of these studies has resulted in confusion concerning the immunologic relationship between these two organisms and the distinction of the two species. In order to better understand, detect and describe *M. genitalium*, monoclonal antibodies directed towards multiple epitopes of *M. genitalium* are described herein. These monoclonal anti-bodies have been used in ELISA and Western blots to demonstrate their specificity for *M. genitalium*. The establishment of major distinguishing antigens of *M. genitalium* is herein described for the purposes of developing rapid and specific diagnosis of infection by this pathogenic mycoplasma species. The ability to distinguish *M. genitalium* from other mycoplasmas is also attained by use of the antibodies described herein.

SUMMARY OF THE INVENTION

Monoclonal antibodies binding *Mycoplasma genitalium* more strongly than *Mycoplasma pneumoniae, Mycoplasma hominis, Mycoplasma orale, Mycoplasma salivarium* and *Acholeplasm laidlawii* are described herein. These monoclonal antibodies are specific for *M. genitalium* antigens and are utilized in immunoassays directed toward the detection of *M. genitalium* infections. Hybridomas producing the above-described monoclonal antibodies have been created and isolated. Certain of these antibodies bind protein antigens, while others bind lipid antigens. In one case a particular antibody apparently has binding affinity for both protein and lipid antigens of *M. genitalium*.

BRIEF DESCRIPTION OF THE PREFERRED EMBODIMENT

The preparation of hybridoma cell lines derived by fusing an immortal cell line and lymphocytes sensitized against the immunogenic preparation can be done by techniques which are well known to those who are skilled in the art. (See, for example, Douillard, J. Y. and Hoffman, T., "Basic Facts About Hybridomas," in: *Compendium of Immunology Vol. II*, L. Schwartz (Ed.) (1981); Kohler, G. and Milstein, C., *Nature.* 256, 495-497 (1975); *European Journal of Immunology*, Volume 6 pp. 511-519 (1976), Koprowski et al., U.S. Pat. No. 4,172,124, Koprowski et al. U.S. Pat. No. 4,196,265, and Wands, U.S. Pat. No. 4,271,145, all of Which are herein incorporated by reference.)

The choice of animal is dependent on the availability of appropriate plasmacytoma lines capable of fusing with lymphocytes thereof. Mouse and rat have been the animals of choice in hybridoma technology, and are preferably used. Humans can also be utilized as sources for sensitized lymphocytes if appropriate immortalized human (or nonhuman) cell lines can be fused therewith.

Injection into the animal can be carried out until the animal serum is positive to the immunogenic preparation. Usually the injecting material is emulsified in Freund's complete adjuvant. The detection of antibodies can be carried out by testing the antisera with appropriately labeled or unlabeled antigen. Lymphocytes can be obtained by removing the spleen of sensitized animals in a sterile fashion and carrying out fusion. Alternatively, lymphocytes can be stimulated or immunized in vitro.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency. Intraspecies hybrids, particularly between like strains, are more common than interspecies fusions; yet either are acceptable. Several cell lines are available, including mutants selected for the loss of ability to secrete myeloma immunoglobulin. Included among these are the following myeloma lines: $MPC_{11}45$-6TG, P3ONS1-1-Ag4-1, P3-X63-Ag8, or mutants thereof such as X63-Ag8.653, SP2-0-Ag14 (all BALB/C derived), Y3-Agl.2.3 (rat), and U266 (human).

Cell fusion can be induced either by virus or polyethylene glycol. Although viruses have been progressively replaced by chemical agents as preferred fusion inducers, they may still be used, including HVJ, Epstein-Barr or Sendai virus. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1,000 to 6,000. In general it gives best results when diluted to 30-50% in saline or serum-free medium. Exposure to 30% PEG at 25° C. for 8 minutes seems best. Extremes of temperature should be avoided and preincubation of each component of the fusion system at 37° C. prior to fusion gives optimum results. The ratio between spleen cells and malignant cells should be optimized to avoid "cell fusion" among spleen cells. Myeloma/spleen cell ratios ranging from 1:2 to 1:10 give good results.

The successfully fused cells can be separated from the myeloma line by any technique available to the art. The most common and preferred method is to choose a malignant line which is Hypoxanthine Guanine Phosphoribosyl Transferase (HGPRT) deficient, which will not grow in an aminopterin-containing medium because of its inability to synthesize purines from thymidine and hypoxanthine. The selection medium used to allow only growth of hybrids is generally composed of hypoxanthine $1 \times 10^{-4}$M, aminopterin $1 \times 10^{-5}$M, and thymidine $3 \times 10^{-5}$M, commonly known as the HAT medium. The fusion mixture can be grown in the HAT-containing culture medium immediately after the fusion or 24 hours later. The feeding schedules usually entail maintenance in HAT medium for two weeks and then feeding with either regular culture medium or hypoxanthine, thymidine containing medium.

The growing colonies are tested for the presence of antibodies that recognize the *M. genitalium* antigenic preparation as well as antigenic fragments from *M. genitalium*. Detection of hybridoma antibodies can be performed using assays where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 5–16 days of cell growth in selected medium. Cloning can be performed by limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semisolid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, intraspecies hybrids may be transferred into animals with inflammatory ascites. Antibody containing ascites can be harvested 8–12 days after intraperitoneal injection. The ascites contain a higher concentration of antibodies but include both monoclonal and immunoglobulins from the inflammatory ascites.

A number of monoclonal antibodies can be obtained by this method, each having different specificity. The specificities can vary from those that recognize only antigens of *M. genitalium* to those recognizing antigens of more than one species of *Mycoplasma* or other related genus.

The obtained monoclonal antibodies are very discriminating between different microorganisms which they specifically bind. The detection of *M. genitalium* infections is carried out by standard immunoassay methodology well known to those with skill in the art. An animal sample, such as a serum sample, feces sample, urine sample, or any other physiological fluid containing or suspected of containing *M. genitalium* antigens is tested by such known immunoassay methodology.

For example, in competitive immunoassay, a sample containing *M. genitalium* antigens is incubated with an anti *M. genitalium* monoclonal antibody or detectably labeled *M. genitalium* antigens. Among the detectable labels usable in the present invention are radiolabels, enzyme labels, chromophoric labels or other labels.

Labels other than radioactive labels might be used since they are well known in generalized binding assay techniques, with the critical limitation, of course, that they do not alter the immunogenicity of *M. genitalium* antigens. Thus, for example, alternatives to isotopic labels may be (a) chromophoric labels such as fluorescent, ultraviolet absorbing or visible light absorbing labels. These are advantageous because of their long shelf life in the absence of radiation; (b) enzyme labels: since specific enzymes can be coupled to other molecules by covalent links, a highly specific enzyme may be covalently reacted. (See, e.g., Schuurs, A. H. W. M. and Van Weemen, B. K. *Clinica Chim. Acta* 81: 1–40 (1977), herein incorporated by reference); and (c) other tracers: free radical labels or bacterial labels can also be used in the present invention.

The general competitive binding assay techniques useful for detection of minute amounts of antigens are well known in the art. Any of these competitive binding assay techniques can be used for the purposes of the present invention. If *M. genitalium* antigen is present in the sample, it will compete with detectably labeled *M. genitalium* antigen for the monoclonal antibody binding sites. The more unknown *M. genitalium* antigen is present, the less the labeled *M. genitalium* antigen will be bound by the antibody.

It is then necessary to determine the distribution of labeled between the free and the bound form. Usually but not always, this requires that the bound fraction be physically separated from the free fraction; a variety of techniques can be used for that purpose. All of these techniques exploit physical-chemical differences between the labeled and its free and bound form. These techniques include adsorption of free antigen to solid phase material, such a cellulose, nitrocellulose membranes, charcoal, silicates or ion exchange resins; precipitation of antigen/antibody complexes by second antibody or Protein A; salting out techniques or organic solvents; adsorption or complexing of antibody to solid phase material; electrophoretic separation on cellulose, starch gel or polyacrylamide gel, and the like.

The choice of technique depends on the speed, simplicity, applicability and cost. It is a simple matter of choice for anyone skilled in the art and therefore, the generalized techniques will not be described in further detail.

Particularly preferred among the aforementioned techniques are the solid phase systems. When the monoclonal antibody is covalently coupled to a insoluble support, both it and the bound complex can readily be separated from the soluble free fraction. A wide variety of solid phase supports have been described which include particles of dextran and nitrocellulose membranes, and continuous surfaces such as polystyrene and polypropylene discs, nitrocellulose membrane or the walls of plastic or glass tubes or slides. Plastic surfaces exhibit adsorptive properties, and simply exposing such surface to an appropriate dilution of the monoclonal antibody will lead to the attachment of a proportion of the antibody molecules thereon. The bond is probably ionic or hydrophobic, and not covalent. Covalent bonding, however, can be readily obtained by the incorporation of cross-linking agents such as glutaraldehyde and other agents in the antibody solution used for the coating.

Coated tube systems offer great convenience in the actual performance of assays and the technique can be widely used in commercial kits.

In one preferred embodiment, the antibody is covalently attached to the inside of a test tube and labeled *M. genitalium* antigen is incorporated in the tube. A single addition of a sample fluid being tested is then added to the test tube. After incubation, the contents of the tube are emptied and the tracer is detected by standard methodology.

A most preferred embodiment is the use of a "sandwich" immunoassay (simultaneous, forward or reverse modes) wherein solid phase bound monoclonal anti *M. genitalium* antibody is incubated with the animal sample containing *M. genitalium* antigen followed (or simultaneously) by incubation with a second anti *M. genitalium* antibody (which may or may not be monoclonal). The second antibody is normally detectably labeled, as for example with an enzyme. Sandwiching of *M. genitalium* antigen occurs only if *M. genitalium* antigen is present in the sample being tested, and detection of the label is therefore an indication of the presence of *M. genitalium* antigen in the sample.

The monoclonal antibody can be attached to a particulate solid phase by any one of a number of techniques designed to yield a covalent link between the protein and the particles, such as for example diazotization or cyanogen bromide. The resulting material is extensively washed to insure that no free monoclonal antibody molecules remain. Alternative approaches include non-covalent binding using bicarbonate buffers (pH 9.6), or the use of antibody entrapped in the interstices of a polyacrylamide gel or covalently bound to magnetic particles. With the latter system, mixing and separation can be simply achieved by the application of magnetic field.

Detection of the label by some physical or chemical means is usually necessary. When the label is an enzyme, the enzyme is assayed by the addition of a substrate which upon reaction releases an ultraviolet or visible light absorbing product. For example the enzyme may be alkaline phosphatase assayed by the hydrolysis of p-nitrophenylphosphate, which releases p-nitrophenol having a large absorption coefficient at 400 nm. Appearance of yellow coloration is a direct indication of the presence of *M. genitalium* antigen in the animal sample.

Still another immunoassay method included in the present invention is the so-called "latex particle agglutination technique." This technique does not involve the use of a detectably labeled *M. genitalium* antigen or enzyme linked technology. See for example Sawai, et al., U.S. Pat. No. 4,118,192 or Hoffman, British Pat. No. 1,384,399. In these techniques monoclonal antibody specific for *M. genitalium* antigen is supported on an insoluble carrier particle, usually a latex particle, thus sensitizing the insoluble particle. The supported monoclonal antibody is then reacted with a sample suspected of containing *M. genitalium* antigen. The sensitized latex agglutinates to a degree which is proportional to the amount of *M. genitalium* antigen present in the sample. The agglutination is followed by irradiating the resulting reaction mixture with light having a wavelength in the range of 0.6–2.4 microns. The determination of absorbance can be performed with a spectrophotometer similar to that used in near infrared spectrometry. Polystyrene latexes or styrene-butadiene latexes can readily be used, however, other particles such as dispersed coccal bacteria, cell membrane fragments, micro particles of inorganic oxides such as silica, silica alumina, and alumina or pulverized minerals, metals and the like are also readily usable. The latex agglutination techniques not only make it possible to determine low concentrations of *M. genitalium* antigen but enable the determination of the *M. genitalium* antigen in trace amounts and with comparable specificity to those of the radio or enzyme immunoassay methodology. The amount of *M. genitalium* antigen can be determined by measuring the absorbance as described above or, alternatively, by measuring the rate of reaction, or the reaction time required for the absorbance to reach a prescribed value.

The Sawai et al. methodology is also applicable in the inhibition of agglutination mode. In this mode, latex particles are coated with *M. genitalium* antigen. The particles are then incubated with monoclonal antibody. The formed complex is mixed with samples suspected of containing *M. genitalium* antigen. If a sample contains *M. genitalium* antigen the latter will compete for the antibody binding site and inhibit the agglutination of the *M. genitalium* antigen-covered latex particles.

The techniques and materials of the present invention for the detection of *M. genitalium* antigen can be readily automated. A noteworthy development in the field of automated radioimmunoassay is the patent of Brooker, et al., U.S. Pat. No. 4,022,577.

Among the kits useful in the present invention are those of the general type described by Szczesniak, U.S. Pat. No. 3,899,298. Such kits comprise a carrier being compartmentalized to receive at least one, or at least two or at least three or more containers and to maintain said containers in closed confinement. A first container may contain purified anti-*M. genitalium* monoclonal antibody, either in solution, in freeze-dried form or covalently bound to the inside thereof, such as for example if such container is a test tube. The monoclonal antibody specific for *Mycoplasma genitalium* antigen is essentially free of binding affinity for *Mycoplasma pneumoniae* antigen, as well as being essentially free of binding affinity for *Mycoplasma hominis, Mycoplasma orale, Mycoplasma salivarium,* and *Acholeplasm laidlawii.* A second container may then contain a second monoclonal anti-*M. genitalium* antibody. Alternatively, another container may contain detectably labeled *M. genitalium* antigen. At the time of testing for *M. genitalium* antigen in the sample, the sample is added to the first container containing the monoclonal antibody, incubated, and then antibody from the second container is added thereto to provide a "sandwich". The antibody in the second container may be detectably labeled as, for example, by a radio label or an enzyme label. Another container in the kit may contain appropriate enzyme substrate in order to carry out the "ELISA" methodology. Any number of variations or permutations consistent with the various techniques for use in the detection of *M. genitalium* antigen can be envisioned for the preparation of a kit. These are all matters of choice, determined by the ease of handling, rapidity and efficiency of the testing.

Quantitative analysis of *M. genitalium* antigen can be carried out by interpolation into a standard curve, as is known in the art. A multiplicity of container means, each one having a different amount of *M. genitalium* antigen can be present in the kit for such a purpose.

In still another embodiment, the monoclonal antibody can be immobilized onto plastic strips which are then brought into contact with the samples suspected of containing *M. genitalium* antigen. Subsequently, the strip is contacted with a solution containing a second, enzyme labeled anti *M. genitalium* antibody; this results in a sandwich forming on the strip. Finally, introduction of the strip into a color developing solution (such as substrate for the enzyme) and detection of color, is a rapid, efficient and inexpensive method for qualitatively, and even roughly quantitatively determining *M. genitalium* antigen in animal samples.

The immunoassay of the present invention uses antibodies which are very discriminating between the different Mycoplasmas. The methodology described herein is far superior in sensitivity and ease to any other known method of *M. genitalium* detection.

The development of specific diagnostic tests for infections of *Mycoplasma genitalium* has become medically desirable. Such specific diagnostic tests as described herein may be developed through the use of monoclonal antibodies specifically binding to *M. genitalium.* The present invention comprises the creation and use of monoclonal antibodies specific for *M. genitalium.* These monoclonal antibodies have a strong binding affinity for *M. genitalium* as compared to their binding affinity for a variety of other *Mycoplasma*-type organisms. Hybrid continuous cell lines (hybridomas) producing these *M. genitalium*-specific antibodies have been isolated.

A method for the immunochemical diagnosis of *M. genitalium* infection in a mammal using the above-described monoclonal antibodies may comprise the steps of: (a) contacting a sample of urogenital fluid (e.g. urine) or tissue (e.g. urethral scrapings or washings) with a monoclonal antibody having the above-described binding properties; (b) measuring the amount of binding between antigens of the sample and said monoclonal antibody; and (c) diagnosing *Mycoplasma genitalium* infection when said amount of binding between the monoclonal antibody and the antigens of the sample is greater than that found between the same monoclonal antibody and a sample of urogenital fluid or tissue from an uninfected mammal (control), and wherein a lesser or equal amount of antibody binding in a test sample compared to uninfected sample binding is indicative of an animal uninfected with *Mycoplasma genitalium.*

Of the monoclonal antibodies described herein some are specific for *M. genitalium* proteinaceous antigens, and some for *M. genitalium* lipid antigens. One particularly interesting hybridoma produced an antibody having a binding affinity for both lipid and proteinaceous antigens of *M. genitalium.* The following examples are intended to illustrate preferred embodiments of the present invention but are not meant to limit the scope of this patent unless specifically otherwise so stated in the claims appended hereto. Hybridomas now deposited with the American Type Culture Collection, (rockville, Md.) are appended by their ATCC deposit numbers. These hybridomas include, by way of example:

H 37.5 $C_9$ (ATCC HB9103)
H 23.3 $D_1$ (ATCC HB9104)
H 37.11 $D_9$ (ATCC HB9105)
H 37.21 $D_{11}$(ATCC HB9106)
H 37.15 $B_6$ (ATCC HB9107)
H 37.15 $F_8$ (ATCC HB9108)
H 23.1 $F_{11}$ (ATCC HB10285).

EXAMPLE 1

Methodology

Immunization of mice

BALB/c female mice (6–8 wk old) were used for all immunizations. For fusion H23, mice were injected intraperitoneally (i.p.) on day 1 with 125 ug *M. genitalium* strain G37 (ATCC 33530) emulsified 1:1 (vol:vol) in Freund's complete adjuvant. On day 9, mice were given i.p. injections of 125 ug strain G37 in saline; 75 ug i.p. and 75 ug intravenously (i.v.). The mouse was sacrificed three days later and the spleen excised and cells thereby hybridized with myeloma cells. The hybridization procedure has been described in Morrison-Plummer, et al. (1983), *J. Immunol. Meth.,* 64, pp 165–178 which is incorporated by reference herein. For fusion H37, mice were immunized on days 1, 15, 73, 80 and 125 with i.p. injections of 100–175 ug *M. genitalium* strain G37 in saline. Hybridization was performed on day 129.

Enzyme-linked immunosorbent assay (ELISA)

A modified ELISA was used for detection of serum and monoclonal antibodies to whole mycoplasma organisms (Morrison-Plummer, et al. (1983), J. Immunol. Meth. V 64, pp 165–178). Organisms were diluted to 26.7 ug protein/ml in phosphate buffered saline (PBS). Each well of Immunolon I microtiter strips (Dynatech Labs), Alexandria, Va.) received 75 ul of organisms. Wells were dried overnight at 37° C. and stored dry at 4° C.

Prior to use, all wells were blocked using PBS supplemented with 1% bovine serum albumin (BSA, Sigma Chemical Co., St. Louis, Mo.). The ELISA procedure has been described (Morrison-Plummer, et al. (1983), *J. Immunol. Meth.* V 64, pp 165–178).

Immunoglobulin isotyping of monoclonal antibody

Monoclonal antibodies were isotyped by ELISA using antimouse isotyping reagents from Zymed Labs, Inc. (San Francisco, Calif.) (Morrison-Plummer, et al. (1983), *J. Immunol. Meth.,* V 64, pp 165–178).

Immunoblot analysis of monoclonal antibodies representative hybridomas are shown which distinguished M. genitalium (species M30 and G37).

TABLE 1

SPECIFICITY OF MONOCLONAL ANTIBODIES
TO M. GENITALIUM PROTEIN ANTIGENS[b]

| Monoclonal[a] antibody | M. genitalium[c] G37 | M30 | Mycoplasma pneumoniae | hominis | orale | salivarium | Acholeplasma laidlawii |
|---|---|---|---|---|---|---|---|
| H23.1F$_{11}$ | .636[d] | .966 | .018 | .010 | .007 | .015 | .011 |
| H23.3D$_1$ (ATCC HB9104) | .348 | .250 | .004 | −.006 | −.009 | .008 | −.007 |
| H23.19H$_{11}$ | .876 | 1.132 | .025 | .007 | .008 | .020 | .017 |
| H23.22C$_9$ | .386 | .465 | .009 | −.001 | .005 | .027 | .001 |
| H37.3C$_6$ | .553 | .646 | .003 | .055 | .012 | .023 | −.029 |
| H37.5C$_9$ | .415 | .232 | .017 | .023 | −.001 | .017 | .003 |
| H37.11D$_9$ (ATCC HB9105) | 1.232 | .392 | .006 | .013 | .014 | .008 | .018 |
| H37.12G$_5$ | .099 | .123 | −.003 | .028 | −.003 | .006 | .010 |
| H37.15F$_8$ (ATCC HB9108) | .333 | .108 | .016 | .055 | .020 | .024 | −.003 |

[a]Monoclonal antibodies were assayed as tissue culture supernatants (antibody concentration estimated to be 1-10 ug/ml).
[b]All antigens were prepared as a constant concentration of 2 ug protein per well.
[c]M. genitalium species G37 and M30.
[d]Values shows represent the mean of triplicate samples. Standard deviation was ≦20% of the mean. Results represent a minimum of three experiments.

Pellets of M. pneumoniae or M. genitalium were resuspended in PBS to an approximate concentration of 4-8 mg/ml. An equal volume of SP buffer (0.1M Tris, pH 6.8; 2% sodium dodecyl sulfate; 20% glycerol; 2% B-mercaptoethanol; 0.02% Bromphenol Blue) was added and the samples boiled for 5 min. They were then microfuged for 5 min to pellet insoluble proteins.

Preparative 7.5% sodium dodeoyl sulfate (SDS)-polyacrylamide gel electrophoresis (PAGE) was performed, each gel containing 2.0-2.5 mg of total mycoplasma proteins. The contents of the gels were then electrophoretically transferred to nitrocellulose membranes (Bio-Rad, Richmond, Calif.) according to the method of Towbin, et al. (Towbin, et al. (1979) Proc. Natl. Acad. Sci., V 76, pp 4350-4354). Molecular weights of proteins were determined by coelectrophoresis of $^{14}$C-labeled molecular weight protein standards (Bethesda Research Lab., Gaithersburg, Md.). For studies of co-migrating proteins in M. pneumoniae and M. genitalium, gels were prepared by aliquoting solubilized preparations of M. pneumoniae and M. genitalium side by side to ensure a similar migration pattern. Antigen-bound nitrocellulose blots were cut into strips to screen individual monoclonal supernatants. To block unbound sites on the nitrocellulose membranes, the strips were incubated 2 h in 3% gelatin in Tris-buffered saline (TBS; 20 mM Tris; 500 mM NaCl; pH 7.5). They were then incubated 1 h at 37° C., or overnight at 25° C. with monoclonal antibody tissue culture supernatants diluted 1:3, 1:10 or 1:20 in TBS+1% gelatin. Prior to and following a 3 h (25° C.) incubation with a 1:2000 dilution of horseradish-peroxidase conjugated anti-mouse Ig (Hyclone, Logan, Utah), blots were washed three times with TBS. The substrate color-developing reagent 4-chloro-1-naphthol (Bio-Rad, Richmond, Calif.) was used to develop the immunoblots.

EXAMPLE 2

Specificity of Antibodies for Mycoplasma Genitalium Proteinaceous Antigens

Monoclonal antibodies to M. genitalium synthesized by hybridomas from two myeloma-spleen cell fusions (H23 and H37) were screened by ELISA for crossreactivity to other species of mycoplasma. In Table 1 nine As the data in Table 1 shows, the listed monoclonal antibodies bind more strongly to M. genitalium than to the other Mycoplasma species. In fact, the data indicates that the specific monoclonal antibodies against M. genitalium antigen are essentially free of binding affinity for Mycoplasma pneumoniae, Mycoplasma hominis, Mycoplasma orale, Mycoplasma salivarium, and Acholeplasm laidlawii.

EXAMPLE 3

Protein Binding Specificity and Isotype of Monoclonal Antibodies

When analyzed by immunoblot, the majority of the monoclonal preparations were reactive to a protein which migrated at 140 kDa (Table 2). One monoclonal antibody identified two proteins which migrated respectively as 31 and 68 kDa, and another bound a 90 kDa protein. Two other monoclonal antibodies bound to a 66 kDa protein.

TABLE 2

REPRESENTATIVE MONOCLONAL ANTIBODIES TO M. GENITALIUM PROTEINS

| Molecular weight of protein[a] | Number of clones | Representative clones | Representative isotype[b] |
|---|---|---|---|
| 31K, 68K | 1 | H37.5C$_9$ | IgG2$_a$ |
| 66K | 2 | H23.3D$_1$ (ATCC HB9104) H23.22C$_9$ | IgG$_1$ IgM |
| 90K[c] | 1 | H37.15B$_6$ | IgG$_3$ |
| 140K | 14 | H37.11D$_9$ (ATCC HB9105) H23.19H$_{11}$ H37.3C$_6$ H37.15F$_8$ (ATCC HB9108) | IgG2$_a$ IgM IgG$_1$ IgG2$_b$ |

[a]Molecular weights determined by immunoblot (K = 1000).
[b]Isotypes determined by microELISA.
[c]Also reacts by microELISA to M. genitalium lipid extracts.

EXAMPLE 4

Monoclonal Antibodies Which Identify Lipid Antigens Specific for M. Genitalium

ELISA screening of H23 and H37 fusions identified three monoclonal antibodies which reacted to chloroform-methanol extracts of M. genitalium. This methodology for lipid antigen preparation has been documented for use with M. pneumoniae (Morrison-Plummer, et al. (1983), *J. Immunol. Meth.* V 64, pp 165-178). As shown in Table 3, monoclonal antibodies H37.21D$_{11}$ (ATCC HB9106), 37.8B$_8$, and 37.15B$_6$ (ATCC HB 9107) reacted to lipid extracts of *M. genitalium* and not to *M. pneumoniae*.

TABLE 3

REACTIVITY OF H37 MONOCLONAL ANTIBODIES TO *M. GENITALIUM* LIPID ANTIGENS

| Monoclonal antibody[a] | *M. genitalium* (strain G37) | | *M. pneumoniae* (strain B16) | |
|---|---|---|---|---|
| | Whole cell[b] | Lipid extract[c] | Whole Cell | Lipid extract |
| H37.8B$_8$ | 1.356 | 1.040 | 0.030 | 0.100 |
| H37.15B$_6$ (ATCC HB9107) | >1.500[d] | >1.500 | 0.140 | 0.069 |
| H37.21D$_{11}$ (ATCC HB9106) | 0.755 | 0.184 | 0.015 | 0.016 |

[a]Monoclonal antibodies were assayed as tissue culture supernatants (antibody concentration estimated to be 1-10 ug/ml).
[b]Whole cell: mycoplasmas were resuspended in PBS, aliquoted at 2 ug/well and air dried.
[c]Lipid extract: chloroform-methanol extraction of whole mycoplasmas, diluted 1:50 in 95% ethanol and dried, 50 ul/well.
[d]Dynatech MR580 MicroElisa Reader does not print readings over 1.500 at 405 nm.

The species specificity of these monoclonal antibodies is further supported by data shown in Table 4.

TABLE 4

SPECIFICITY OF MONOCLONAL ANTIBODIES TO *M. GENITALIUM* LIPID ANTIGENS[a]

| Monoclonal antibody[b] | Mycoplasma | | | | Acholeplasma |
|---|---|---|---|---|---|
| | genitalium | pneumoniae | hominis | orale | salivarium | laidlawii |
| H37.8B$_8$ | .748[c] | .016 | .025 | .031 | .056 | .026 |
| H37.15B$_6$ (ATCC HB9107) | .046 | .055 | .011 | .066 | .031 | .002 |
| H37.21D$_{11}$ (ATCC HB9106) | .177 | .024 | .028 | .032 | .048 | .049 |

[a]All antigens were prepared as whole organisms and at a constant concentration of 2 ug protein per well.
[b]Monoclonal antibodies were assayed as tissue culture supernatants (antibody concentration estimated to be 1-10 ug/ml).
[c]Values shown represent the mean of triplicate samples. Standard deviation was ≦20% of the mean. Results represent a minimum of three experiments.

Interestingly, monoclonal antibody H37.15B$_6$ (ATCC HB 9107) reacts both to a 90 kDa protein by immunoblot as well as to the lipid preparation by ELISA (Tables 2 and 3). Since it is highly unlikely that proteins could be present in the lipid preparation (Bligh, et al. (1959), *Can. J. Biochem.*, V 37, pp 911-917) (Morrison-Plummer, et al. (1983), *J. Immunol. Meth.* V 64, pp 165-178), this monoclonal antibody may bind to a common epitope such as a carbohydrate linked to both the protein and lipid antigens. It alternatively may be that small amounts of antigenic lipid are part of the 90 kDa protein.

EXAMPLE 5

Sensitivity of Monoclonal Antibodies to Mycoplasma Antigens

The uniqueness of the determinants to which monoclonal antibody from clone H37.15B$_6$ (ATCC HB9107) binds appears to result in a high level of reactivity to *M. genitalium* as shown in Table 5.

TABLE 5

SENSITIVITY OF MONOCLONAL ANTIBODIES FOR *M. GENITALIUM*

| Monoclonal antibody | Mycoplasma genitalium[a] | | | | | Antigenic Determinant |
|---|---|---|---|---|---|---|
| | 1000 ng | 50 ng | 10 ng | 5 ng | 1 ng | |
| H37.5C$_9$ | .828 | .601 | .169 | .097 | .034 | 68 kDA, 31 kDa |
| H37.6D$_9$ | 1.120 | 1.059 | .219 | .142 | .050 | 140 kDa |
| H37.8B$_8$ | 1.5 | 1.5 | .497 | .145 | .011 | lipid |
| H37.11D$_9$ | 1.276 | 1.095 | .267 | .113 | .020 | 140 kDa |

TABLE 5-continued

SENSITIVITY OF MONOCLONAL ANTIBODIES FOR *M. GENITALIUM*

| Monoclonal antibody | Mycoplasma genitalium[a] | | | | | Antigenic Determinant |
|---|---|---|---|---|---|---|
| | 1000 ng | 50 ng | 10 ng | 5 ng | 1 ng | |
| H37.15B$_6$ | 1.500 | 1.500 | .554 | .313 | .041 | 90 kDa, lipid |
| H37.21D$_{11}$ | .335 | .174 | .006 | .021 | .013 | lipid |

[a]*Mycoplasma genitalium* strain G37 solubilized in 1% SDS and aliquoted at dilutions of 1000 ng to 1 ng per microtiter well and air dried.
[b]Monoclonal antibodies were assayed as tissue culture supernatants (antibody concentration estimated to be 1-10 ug/ml).

Solubilized *M. genitalium* was detectable at 5 ng/microtiter well. This type of assay could be adapted for detection of antigens in vaginal or urethral swabs comprising urogenital fluid or tissue samples (solubilization of the swab sample and coating onto microELISA wells as antigen for the ELISA).

EXAMPLE 6

Sandwich Elisa's and *M. Genitalium* Detection

Sandwich ELISA's are frequently used to facilitate monoclonal antibody detection of small quantities of antigen. As shown in Table 6, this type of assay is easily performed using monoclonal antibody coated microELISA wells.

TABLE 6

Sandwich ELISA using H37.11D9 (ATCC HB9105)
(anti-140 kDa) to detect *M. genitalium*[a]

*Mycoplasma genitalium*

| 50 ng | 10 ng | 1 ng | 0.1 ng |
|---|---|---|---|
| .765 ± .055 | .363 ± .15 | .142 ± .022 | .095 ± .055 |

[a]ELISA microtiter wells were coated with 10 ug Protein A- Sepharose purified monoclonal antibody H37.11D9 (ATCC HB9105). Wells were blocked with PBS + 1% BSA for 1 h at 37° C. *M. genitalium* was solubilized in 1% SDS and was diluted in PBS to give a final concentration of 50, 10, 1, and 0.1 ng/50 ul/microtiter well. Followintg a 1 h incubation at 37° C., wells were washed with PBS (4×), and 50 ul of a 1:10,000 dilution of immune rabbit serum (anti-*M. genitalium*) followed by washing with PBS (4×). Alkaline phosphatase conjugated goat anti-rabbit IgG (Hyclone Laboratories; Logan, Utah) was diluted 1:1000 in PBS + 1% BSA and 50 ul was added per well. Following a 2 h incubation at 37° C., wells were washed with PBS (3×) and H2O (2×), and p-nitrophenyl phosphate substrate buffer was added. Optical density readings were taken at 405 nm using a microELISA reader.

Solubilized *M. genitalium* was detected at 1 ng/well. The probe was polyclonal rabbit anti-*M. genitalium* serum diluted 1:10,000 in PBS-BSA. This assay may be performed using single or multiple preparations of monoclonal antibodies. The monoclonal antibodies may additionally be directly labeled with an enzyme (alkaline phosphatase or horseradish peroxidase) and used in a direct or sandwich ELISA. Directly conjugating the monoclonal antibody alleviates the need for commercially prepared anti-mouse or anti-rabbit conjugates (as used in Tables 5 and 6, respectively). This procedure also reduces the time it takes to perform the assay.

The attachment of single or pooled combinations of highly specific monoclonal antibodies to solid matrixes may allow for a sensitive assay to detect *M. genitalium* infections in patients. This would be a very effective and important tool since many patients suffering from vaginitis or urethritis may harbor known mycoplasma species (as mentioned in the introduction) which are a part of their "natural" flora. A probe specific for *M. genitalium* which would singularly detect its presence even in the midst of other mycoplasma species would aid in the diagnosis of the pathogen and patient treatment.

Changes may be made in the construction, operation and arrangement of the various specific antibodies, steps and procedures described herein without departing from the concept and scope of the invention as defined in the following claims.

What is claimed is:

1. A monoclonal antibody produced by a hybridoma ATCC HB9105 or ATCC HB9108 having binding specificity for non-crossreactive epitopes of a 140 kD *Mycoplasma genitalium* antigen and does not bind to *Mycoplasma pneumoniae, Mycoplasma hominis, Mycoplasma orale, Mycoplasma salivarium* and *Acholeplasm laidlawii*, in an immunoassay directed toward detection of *Mycoplasma genitalium*.

2. A hybridoma comprising hybridoma ATCC HB9105 or ATCC HB9108 that produces monoclonal antibody against non-crossreactive epitopes of a 140 kD *Mycoplasma genitalium* antigen, said hybridoma being a cell hybrid of a spleen cell from an animal immunized with *Mycoplasma genitalium*, and a myeloma from the same animal species as the spleen cell or from an animal species whose cells will hybridize with said spleen cell, said antibody having specific binding for *M. genitalium* and does not bind to *M. pneumoniae, M. hominis, M. orale, M. salivarium*, or *Acholeplasm laidlawii*.

3. A method for the immunochemical diagnosis of *Mycoplasma genitalium* infection in a mammal comprising:

contacting a biological sample from the mammal with a monoclonal antibody produced by a hybridoma ATCC HB9105 or ATCC HB9108 having specific binding for non-crossreactive epitopes of *Mycoplasma genitalium* and does not bind to antigens of *Mycoplasma pneumoniae, Mycoplasma hominis, Mycoplasma orale, Mycoplasma salivarium* and *Acholeplasm laidlawii*;

measuring the amount of binding between antigens of the sample and said monoclonal antibody by a binding assay or a sandwich ELISA binding assay; and diagnosing *Mycoplasma genitalium* infection when said amount of specific binding is greater than that found between the same monoclonal antibody and a biological sample from an uninfected mammal, and wherein a lesser amount of antibody binding in a test sample compared to uninfected sample binding is indicative of an animal uninfected with *Mycoplasma genitalium*.

4. A hybridoma according to claim 2, that produces a monoclonal antibody capable of binding to protein antigen of *Mycoplasma genitalium* said hybridoma being ATCC HB9105.

5. A hybridoma according to claim 2, that produces a monoclonal antibody capable of binding to a protein antigen of *Mycoplasma genitalium* said hybridoma being ATCC HB9108.

6. A monoclonal antibody, according to claim 1, capable of binding to a protein antigen of *Mycoplasma genitalium* said monoclonal antibody being produced by a hybridoma ATCC HB9105.

7. A monoclonal antibody capable of binding to a protein antigen of *Mycoplasma genitalium*, according to claim 1, said monoclonal antibody being produced by a hybridoma ATCC HB9108.

8. A method for the immunochemical diagnosis of *Mycoplasma genitalium* infection in a mammal comprising:

(a) contacting urogenital fluid or tissue samples from the mammal with a monoclonal antibody binding to protein non-crossreactive antigenic epitopes of *Mycoplasma genitalium*, said monoclonal antibody being produced by a hybridoma ATCC HB9105 or ATCC HB9108;

(b) measuring the amount of binding between antigens of the sample and said monoclonal antibody; and (c) diagnosing *Mycoplasma genitalium* infection when said amount of binding is greater than that found between the monoclonal antibody and a sample of urogenital fluid or tissue from an uninfected mammal, and wherein a lesser or equal amount of antibody binding in a test sample compared to uninfected sample is indicative of an animal uninfected with *Mycoplasma genitalium*.

9. A method for the immunochemical diagnosis of *Mycoplasma genitalium* infection in a mammal, comprising:

(a) contacting a body fluid or tissue sample of a mammal with a monoclonal antibody binding to a non-crossreactive antigen of *Mycoplasma genitalium*, said monoclonal antibody being produced by a hybridoma clone ATCC HB9105 or ATCC HB9108;

(b) measuring the amount of binding between antigens of the sample and said monoclonal antibody by a competitive binding assay or a sandwich ELISA binding assay; and (c) diagnosing *Mycoplasma genitalium* infection when said amount of binding is greater than that found with a body fluid or tissue sample from an uninfected mammal, and wherein a lesser amount of antibody binding in a test sample compared to uninfected sample is indicative of an animal uninfected with *Mycoplasma genitalium.*

10. A kit useful for the detection of a *Mycoplasma genitalium* antigen in a sample which comprises:

a carrier being compartmentalized to receive one or more container means in close confinement therein;

a first container means containing a non-crossreactive monoclonal antibody produced by a hybridoma ATCC HB9105 or ATCC HB9108 which is specific for a 140 kD *Mycoplasma genitalium* antigen and does not bind to *Mycoplasma pneumoniae* antigen; and a second container means comprising a detectably labeled non-crossreactive monoclonal antibody produced by a hybridoma ATCC HB9105 or ATCC HB9108 which is specific for a 140 kD *Mycoplasma genitalium* antigen, and does not bind to *Mycoplasma pneumoniae* antigen.

11. The kit of claim 10 wherein said monoclonal antibody in said first container means is immobilized on said container means.

12. The kit of claim 10 wherein said antibody in said second container is labeled with a radiolabel, an enzyme label or a chromophore.

13. The kit of claim 10 which also comprises a multiplicity of container means each containing therein different amounts of a 140 kD *Mycoplasma genitalium* antigen.

14. The kit of claim 10 wherein said first or second container means is a tube.

15. The method of claim 3, wherein the monoclonal antibody is produced by a hybridoma ATCC HB9105.

16. A process for determining the presence of *Mycoplasma genitalium* antigen in an animal fluid using a monoclonal antibody capable of specifically binding to *Mycoplasma genitalium* comprising the steps:

(a) contacting a sample of the animal fluid with a soluble first monoclonal antibody produced by a hybridoma ATCC HB9105 or ATCC HB9108 specifically binding to non-crossreactive epitopes of a 140 kD *Mycoplasma genitalium* antigen and does not bind to *Mycoplasma pneumoniae* to form a soluble complex with any *Mycoplasma genitalium* antigen present in said sample, wherein said first monoclonal antibody is labeled with a radioactive substance, an enzyme or a chromophore;

(b) contacting the soluble complex with a second monoclonal antibody produced by a hybridoma ATCC HB9105 or ATCC HB9108 specifically binding to *Mycoplasma genitalium* antigen, and does not bind to *Mycoplasma pneumoniae,* wherein said second monoclonal antibody is bound to an insoluble solid carrier, to form an insoluble complex of said first monoclonal antibody, said antigen and said second monoclonal antibody bound to said carrier;

(c) separating said solid carrier;

(d) measuring label associated with the solid carrier; and (e) relating said measured label with an amount of label measured for an antigen-free control sample prepared in accordance with steps (a)–(d) to determine the presence of antigen in said fluid sample.

17. The method of claim 3, wherein the monoclonal antibody is defined further as being produced by hybridoma ATCC HB9108.

* * * * *